(12) United States Patent
Gadda et al.

(10) Patent No.: US 11,628,013 B2
(45) Date of Patent: Apr. 18, 2023

(54) SYSTEMS AND METHODS FOR MONITORING PATIENT MOTION DURING A MEDICAL PROCEDURE

(71) Applicant: INTUITIVE SURGICAL OPERATIONS, INC., Sunnyvale, CA (US)

(72) Inventors: Teresa G. Gadda, Palo Alto, CA (US); Troy K. Adebar, Mountain View, CA (US); Cristian Bianchi, Mountain View, CA (US); Vincent Duindam, San Francisco, CA (US); Timothy D. Soper, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 892 days.

(21) Appl. No.: 16/327,219

(22) PCT Filed: Aug. 16, 2017

(86) PCT No.: PCT/US2017/047172
§ 371 (c)(1),
(2) Date: Feb. 21, 2019

(87) PCT Pub. No.: WO2018/038999
PCT Pub. Date: Mar. 1, 2018

(65) Prior Publication Data
US 2019/0192234 A1 Jun. 27, 2019

Related U.S. Application Data

(60) Provisional application No. 62/378,389, filed on Aug. 23, 2016.

(51) Int. Cl.
*A61B 34/20* (2016.01)
*A61B 34/37* (2016.01)
(Continued)

(52) U.S. Cl.
CPC .............. *A61B 34/20* (2016.02); *A61B 34/35* (2016.02); *A61B 34/37* (2016.02); *A61B 34/25* (2016.02);
(Continued)

(58) Field of Classification Search
CPC ......... A61B 34/20; A61B 34/35; A61B 34/37; A61B 34/25; A61B 34/30; A61B 90/37;
(Continued)

(56) References Cited

U.S. PATENT DOCUMENTS 6,380,732 B1 4/2002 Gilboa et al.
6,389,187 B1 5/2002 Greenaway et al.
(Continued)

FOREIGN PATENT DOCUMENTS

CN 103211654 A 7/2013
CN 105105846 A 12/2015
(Continued)

OTHER PUBLICATIONS

Extended European Search Report for Application No. EP17844151.5 dated Mar. 3, 2020, 14 pages.
(Continued)

*Primary Examiner* — Basil T. Jos
(74) *Attorney, Agent, or Firm* — Haynes and Boone, LLP

(57) ABSTRACT

A method of monitoring a medical instrument during a medical procedure includes: receiving state information from a control system in communication with the medical instrument; detecting, by the control system, motion of at least a portion of the medical instrument; comparing the detected motion of the at least the portion of the medical instrument with a threshold motion value based on the state information received from the control system; determining, based on the detected motion exceeding the threshold motion value, significant movement of a patient has
(Continued)

occurred; providing a system response based on determining significant movement of the patient has occurred; comparing the detected motion with a threshold control value, wherein the threshold control value is higher than the threshold motion value; and disregarding, when the detected motion is higher than the threshold control value, motion commands received from a master assembly.

19 Claims, 11 Drawing Sheets

(51) Int. Cl.
    *A61B 34/35*     (2016.01)
    *A61B 34/30*     (2016.01)
    *A61B 34/00*     (2016.01)
    *A61B 90/00*     (2016.01)
    *A61B 34/10*     (2016.01)
    *A61B 17/00*     (2006.01)

(52) U.S. Cl.
    CPC .............. *A61B 34/30* (2016.02); *A61B 90/37* (2016.02); *A61B 2017/00809* (2013.01); *A61B 2034/105* (2016.02); *A61B 2034/2051* (2016.02); *A61B 2034/2059* (2016.02); *A61B 2034/2061* (2016.02); *A61B 2034/301* (2016.02); *A61B 2090/365* (2016.02); *A61B 2090/371* (2016.02); *A61B 2090/374* (2016.02); *A61B 2090/3762* (2016.02)

(58) Field of Classification Search
    CPC .... A61B 2017/00809; A61B 2034/105; A61B 2034/2051; A61B 2034/2059; A61B 2034/2061; A61B 2034/301; A61B 2090/365; A61B 2090/371; A61B 2090/374; A61B 2090/3762; A61B 5/065; A61B 5/1126; A61B 5/113; A61B 1/2676; A61B 2017/00119; A61B 2017/00123; A61B 2034/102; A61B 2034/2065
    See application file for complete search history.

(56) References Cited

U.S. PATENT DOCUMENTS

| | | | |
|---|---|---|---|
| 7,316,681 | B2 | 1/2008 | Madhani et al. |
| 7,772,541 | B2 | 8/2010 | Froggatt et al. |
| 8,900,131 | B2 | 12/2014 | Chopra et al. |
| 9,259,274 | B2 | 2/2016 | Prisco et al. |
| 9,452,276 | B2 | 9/2016 | Duindam et al. |
| 2004/0236352 | A1* | 11/2004 | Wang ................ A61B 34/70 606/1 |
| 2006/0013523 | A1 | 1/2006 | Childlers et al. |
| 2006/0058919 | A1 | 3/2006 | Sommer |
| 2008/0262297 | A1 | 10/2008 | Gilboa et al. |
| 2009/0192524 | A1 | 7/2009 | Itkowitz et al. |
| 2011/0319910 | A1 | 12/2011 | Roelle et al. |
| 2013/0204124 | A1* | 8/2013 | Duindam ........... A61B 17/3468 600/424 |
| 2014/0039306 | A1 | 2/2014 | Klinder et al. |
| 2016/0000516 | A1 | 1/2016 | Cheng et al. |
| 2016/0113728 | A1 | 4/2016 | Piron et al. |

FOREIGN PATENT DOCUMENTS

| | | |
|---|---|---|
| EP | 2772210 A2 | 9/2014 |
| EP | 3405134 A1 | 11/2018 |
| EP | 3478149 A1 | 5/2019 |
| WO | WO-2005084570 A1 | 9/2005 |
| WO | WO-2012158324 A2 | 11/2012 |

OTHER PUBLICATIONS

International Preliminary Report on Patentability for Application No. PCT/US2017/047172, dated Mar. 7, 2019, 12 pages.

International Search Report and Written Opinion for Application No. PCT/US2017/047172, dated Nov. 24, 2017, 16 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

SYSTEMS AND METHODS FOR MONITORING PATIENT MOTION DURING A MEDICAL PROCEDURE

RELATED APPLICATIONS

This patent application is the U.S. national phase of International Application No. PCT/US2017/047172, filed Aug. 16, 2017, which designated the U.S. and claims priority to and the benefit of the filing date of U.S. Provisional Patent Application 62/378,389, entitled "SYSTEMS AND METHODS FOR MONITORING PATIENT MOTION DURING A MEDICAL PROCEDURE," filed Aug. 23, 2016, all of which are incorporated by reference herein in their entirety.

FIELD

The present disclosure is directed to systems and methods for monitoring the motion of a patient or of a medical system relative to the patient during a medical procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. Other minimally invasive techniques may include the user of relatively rigid devices manipulated within the patient anatomy. Control of such an elongate device by medical personnel involves the management of several degrees of freedom including at least the management of insertion and retraction of the elongate device as well as steering of the device. In addition, different modes of operation may also be supported.

During a medical procedure the patient, although likely anesthetized, may move. For example, an involuntary bodily movement may occur, or the patient may be bumped or otherwise moved by an operator or another person present in the surgical environment. Additionally, the minimally invasive system may be moved relative to the patient. Such movements can cause complications during the minimally-invasive procedures, including image-guided medical procedures.

Accordingly, it would be advantageous to provide improved methods and systems for monitoring patient motion during a medical procedure.

SUMMARY

The embodiments of the invention are best summarized by the claims that follow the description.

Consistent with some embodiments, a method of monitoring a medical instrument during a medical procedure involving motion of the medical instrument is disclosed. The method may include receiving state information from a control system in communication with the medical instrument; detecting motion of at least a portion of the medical instrument and comparing the motion of the portion of the medical instrument with a threshold motion value that is based on the state information received from the control system. The method may further include generating a communication message for presentation in a display system based on the comparison of the motion with the threshold motion value. Other embodiments of this aspect include corresponding computer systems, apparatus, and computer programs recorded on one or more computer storage devices, each configured to perform the actions of the methods.

Consistent with some embodiments, a teleoperated medical system is disclosed. The teleoperated medical system may include a teleoperational, elongate medical instrument, a master assembly configured to receive commands from a system operator to manipulate the medical instrument, and a control system in communication with the master assembly and the medical instrument. The control system may be adapted to perform operations including receiving state information from a control system in communication with the medical instrument, detecting motion of at least a portion of the medical instrument, and comparing the motion of the portion of the medical instrument with a threshold motion value that is based on the state information received from the control system. The control system may be adapted to generate a communication message for presentation to an operator based on the comparison of the motion with the threshold motion value.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 5A:
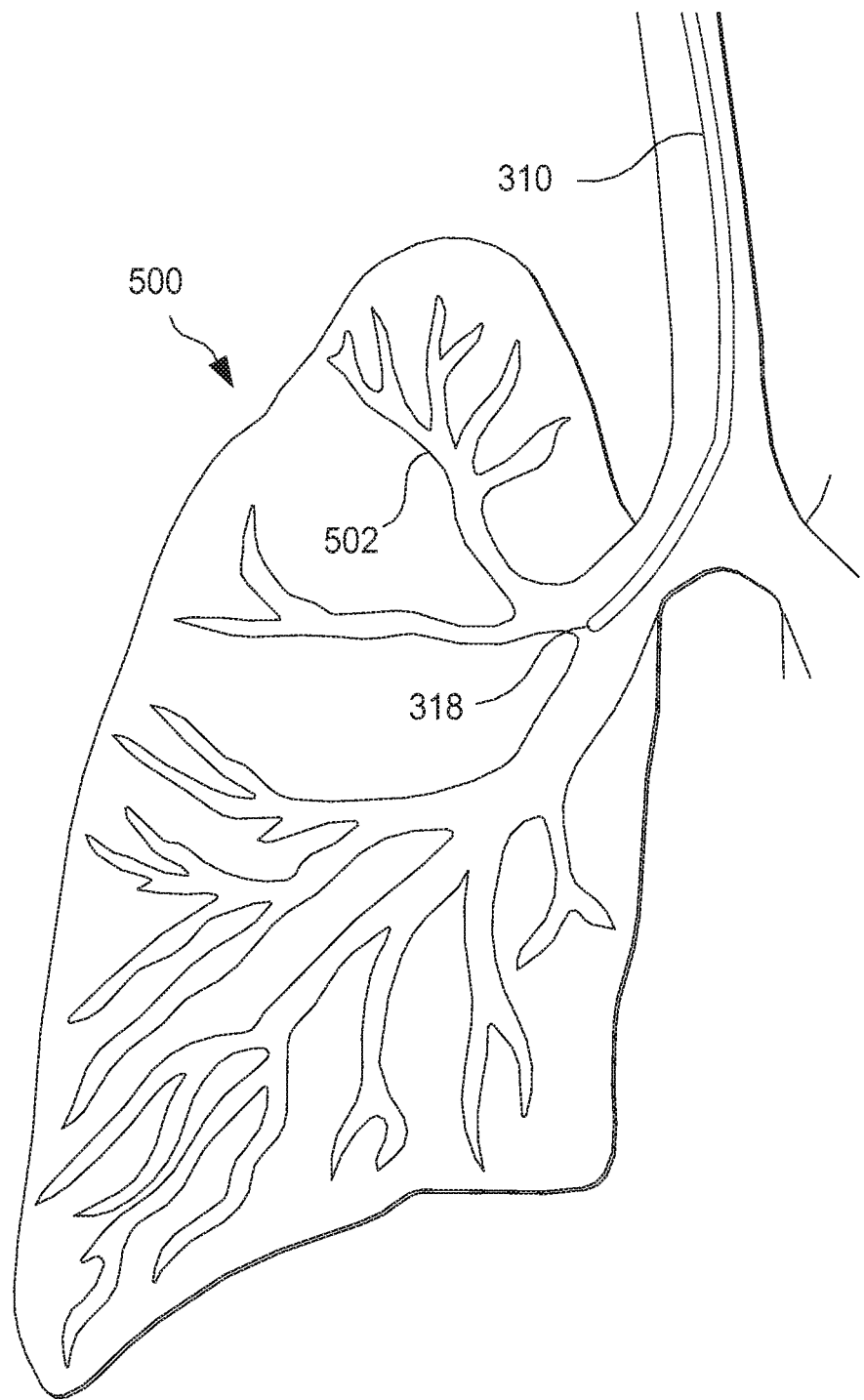
Figure 5B:
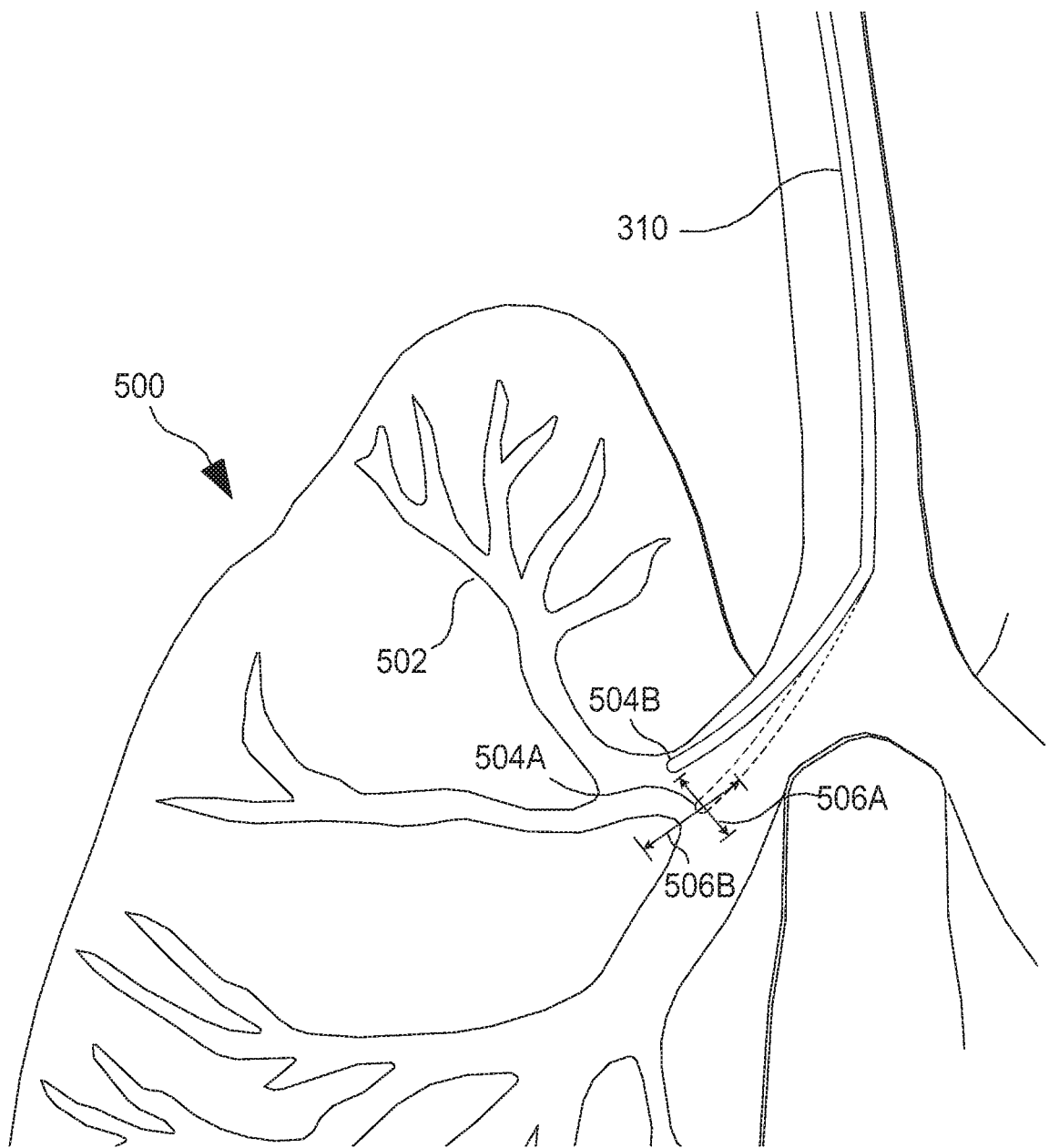
Figure 5C:
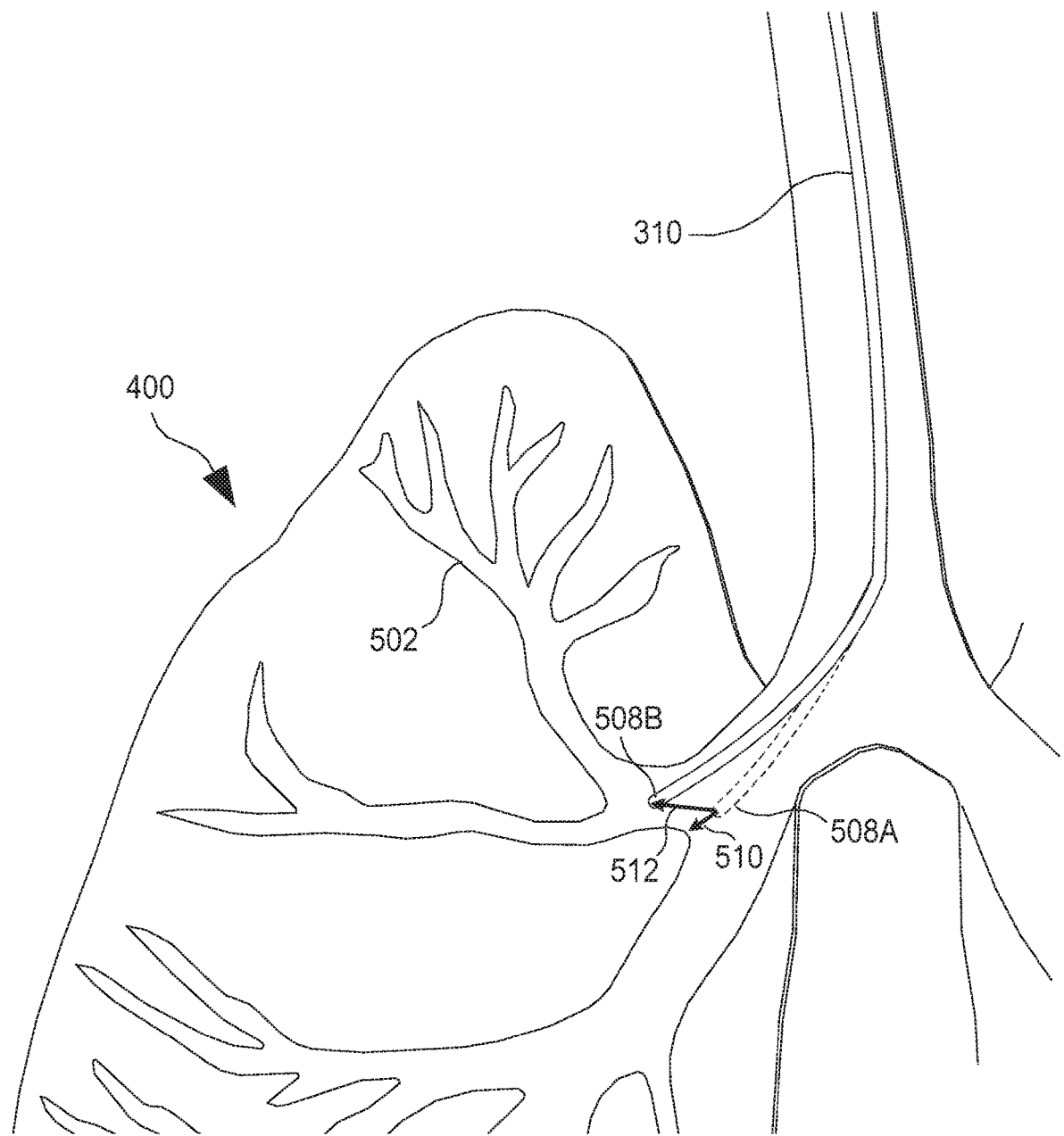

FIGS. 5A, 5B, and 5C illustrate the distal end of the medical instrument systems of FIGS. 2A-C, 3A, and 3B, during use within a human lung according to some embodiments.

Figure 6A:
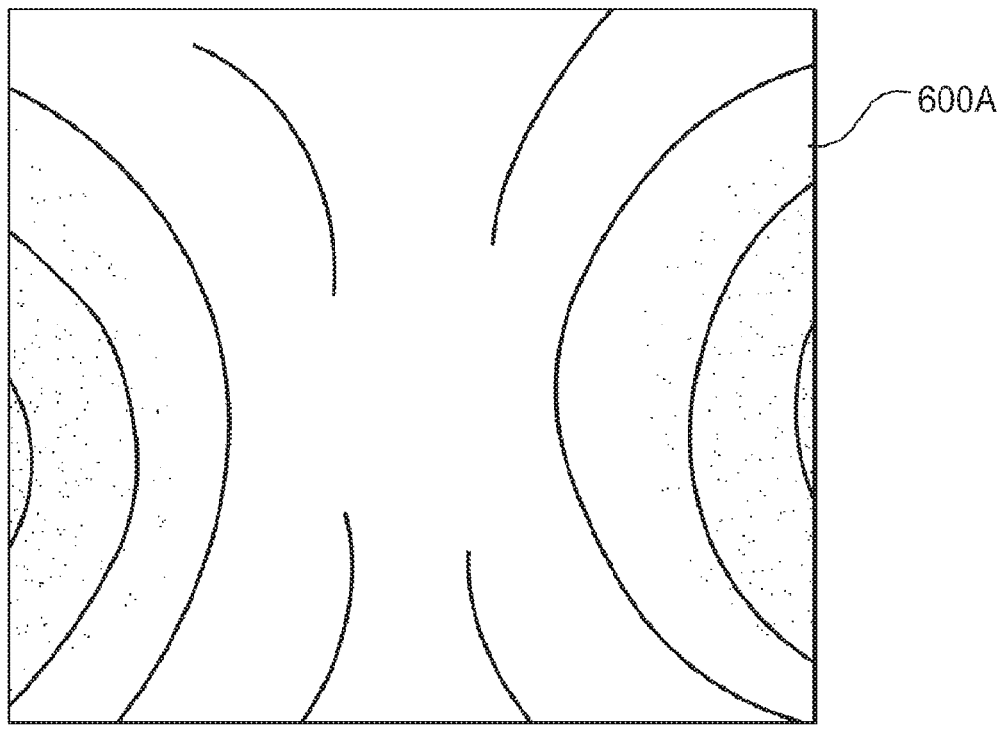
Figure 6B:
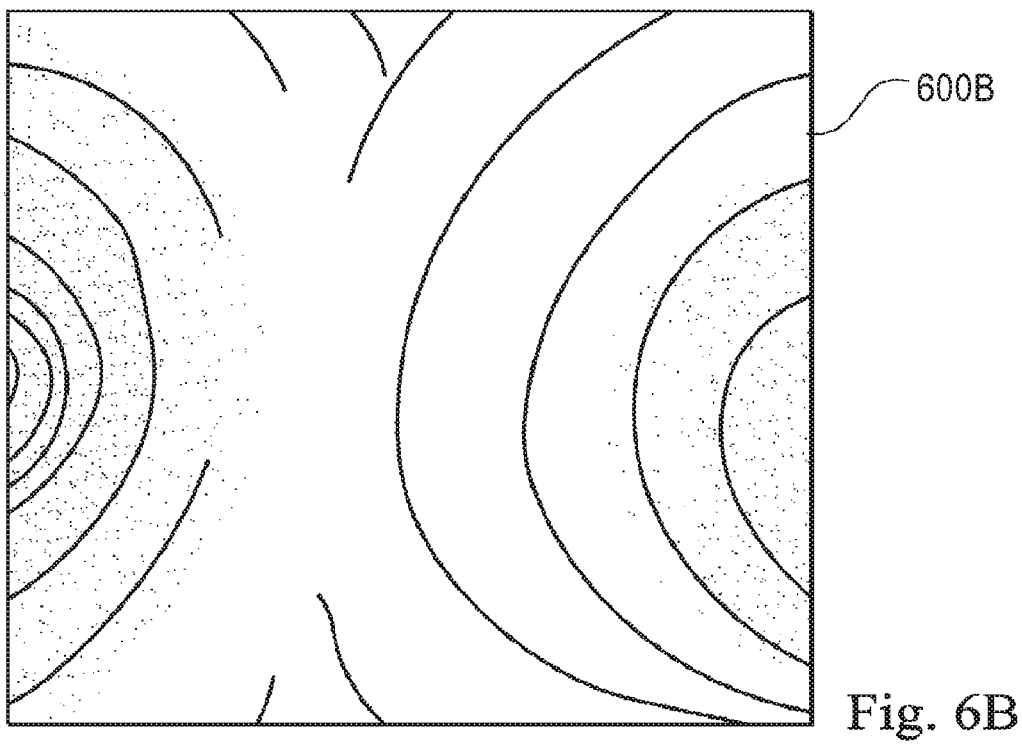

FIGS. 6A and 6B illustrate images that may be used in identifying patient motion patient according to some embodiments.

Figure 7:
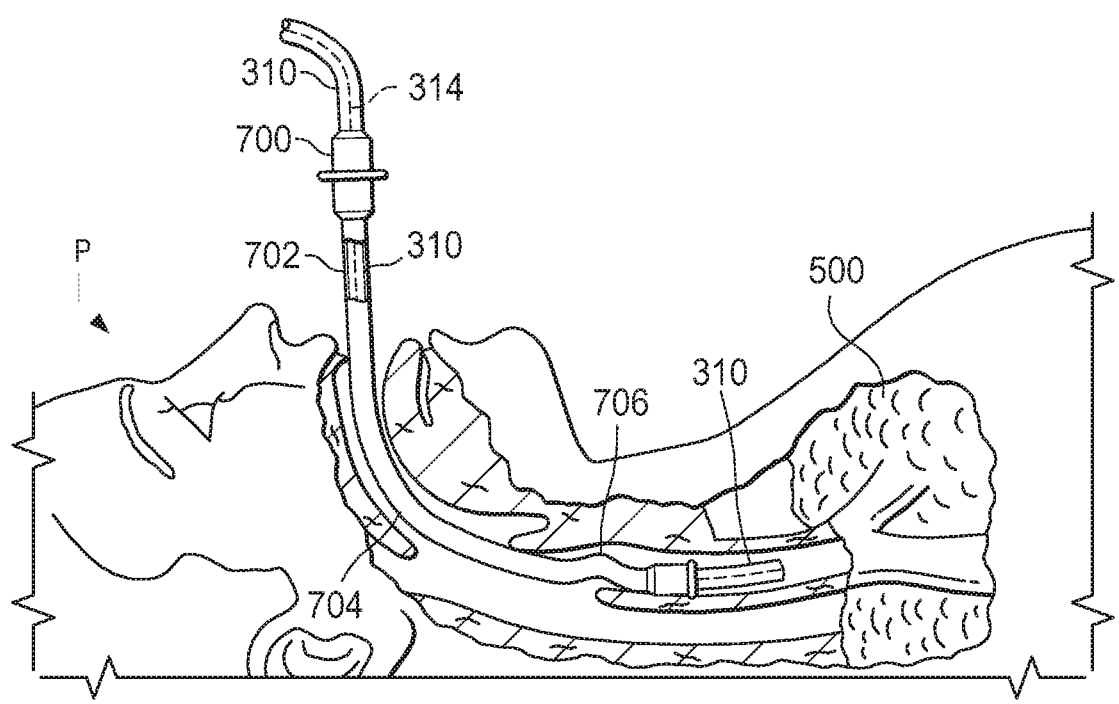

FIG. 7 depicts simplified diagram of a side view of a patient having an endotracheal tube inserted to facilitate use to the medical instrument system according to some embodiments.

Figure 8:
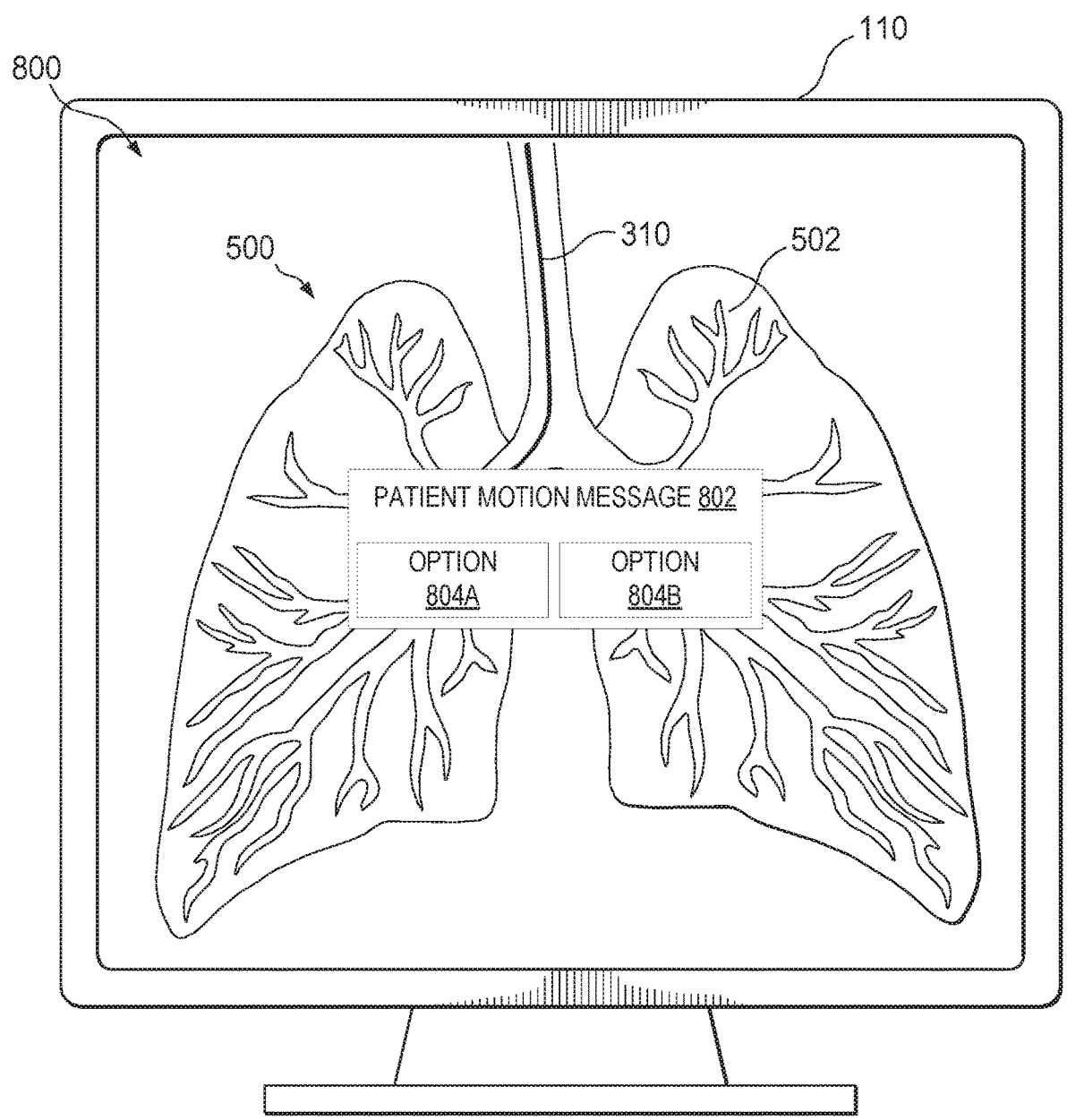

FIG. 8 depicts a user interface according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their position, orientation, and/or pose in three-dimensional space. As used herein, the term "position" refers to the location of an object or a portion of an object in a three-dimensional space (e.g., three degrees of translational freedom along Cartesian X, Y, and Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

The disclosure is generally directed to methods and systems for monitoring the motion of a patient undergoing a medical procedure. In some approaches a dedicated device may be used to monitor a patient P. Embodiments of the present disclosure utilize information from assemblies and instruments that have a primary purpose other than monitoring patient motion. Accordingly, embodiments of the present disclosure may obviate the need of a dedicated patient motion monitoring device by enabling other systems and devices to secondarily provide patient motion monitoring means. The principles of the present disclosure may also be applied to dedicated devices to improve their accuracy and performance in monitoring patient motion.

Figure 1:
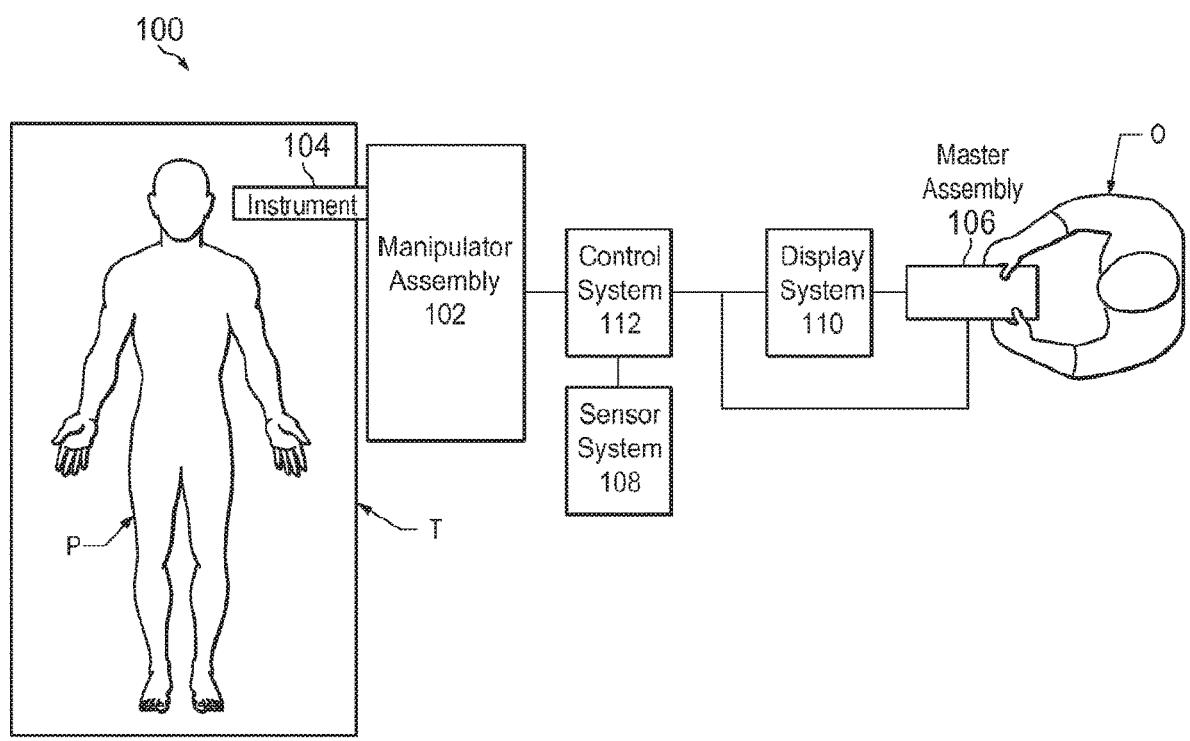
FIG. 1 is a simplified diagram of a teleoperated medical system according to some embodiments.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. An input control device or master assembly 106 allows an operator O (e.g., a surgeon, a clinician, or a physician as illustrated in FIG. 1) to control teleoperational manipulator assembly 102 and, in some embodiments, to view the interventional site.

Master assembly 106 may be located at a physician's console which is usually located in the same room as operating table T. However, it should be understood that operator O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to the medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104. The sensor system 108 may include a plurality of sensors disposed along a kinematic chain of the manipulator assembly 102, in some embodiments.

Teleoperated medical system 100 also includes a display system 110 for displaying an image or representation of the surgical site and medical instrument 104 generated by subsystems of sensor system 108. The display system 110 may further be used to render communications for presentation to the operator O. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image or images of a surgical site and provides the image(s) to the operator or operator O through one or more displays of medical system 100, such as one or more displays of display system 110. The concurrent image may be, for example, a two- or three-dimensional image captured by an endoscope or other medical instrument positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or, a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of an operator that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a distal tip of medical instrument 104. Some embodiments may display both a virtual navigational image and a captured image, which correspond when the model is accurately registered to the patient during the procedure. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include a control system 112. Control system 112 includes at least one memory and at least one computer processor (not shown) for effecting control between medical instrument 104, master assembly 106, sensor system 108, and display system 110, and/or other components of the medical system 100. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during a respiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensors, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional components and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated with the manipulator assembly/assemblies or they may be positioned in separate locations. Multiple master assemblies allow more than one operator to control one or more teleoperational manipulator assemblies in various combinations.

Figure 2A:
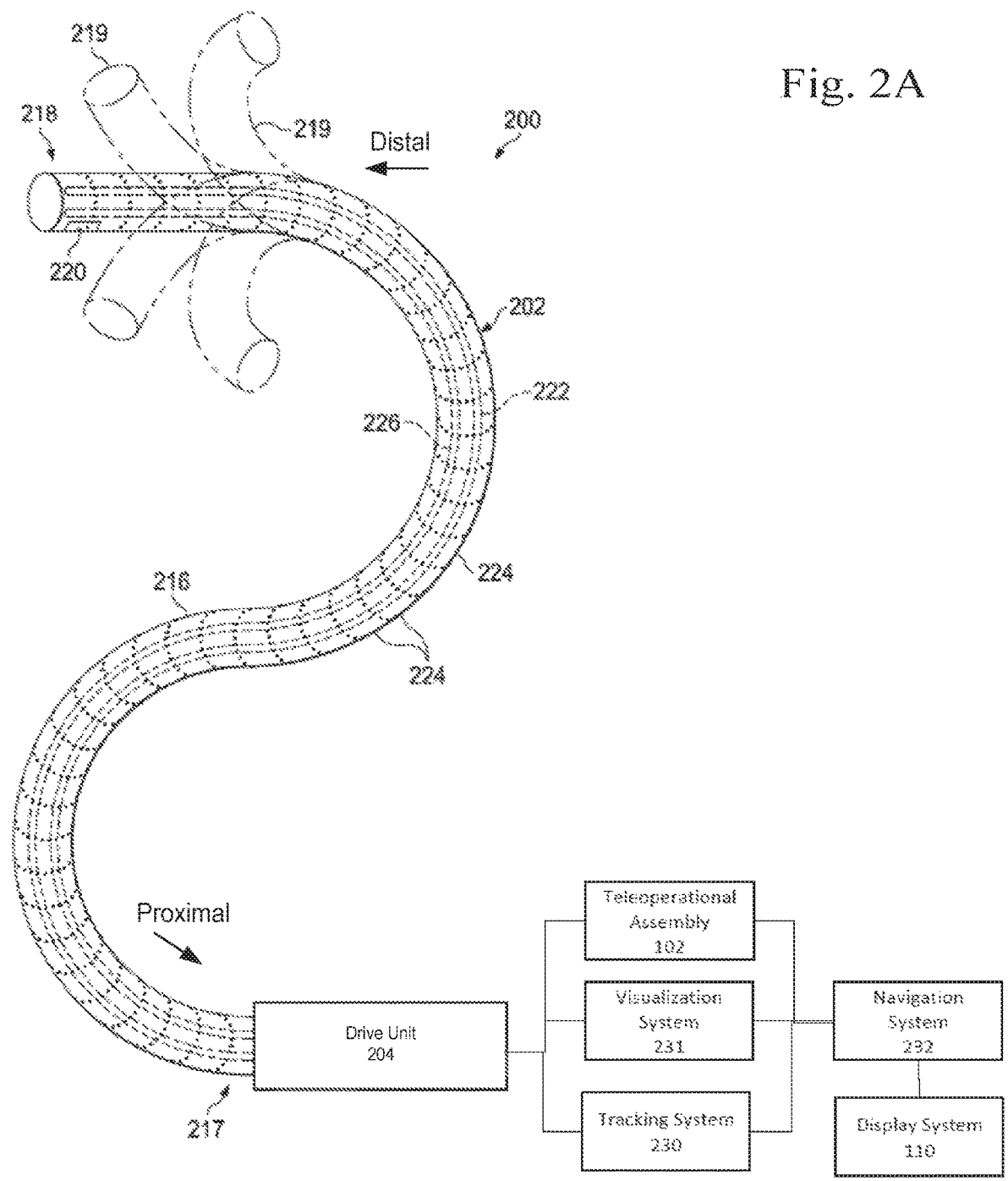
FIG. 2A is a simplified diagram of a medical instrument system according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally, medical instrument system 200 may be used to gather (i.e., measure) a set of data points corresponding to locations within anatomic passageways of a patient, such as patient P.

Figure 2B:
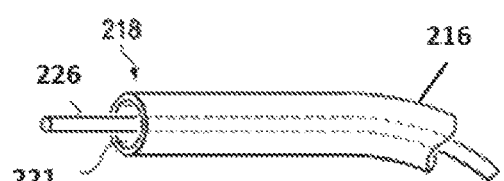
FIG. 2B is a simplified diagram of a medical instrument system with an extended medical tool according to some embodiments.

The medical instrument system 200 of FIGS. 2A and 2B includes elongate device 202, such as a flexible catheter, coupled to a drive unit 204. The drive unit 204 may include a plurality of actuators that can be controlled to steer a distal portion of the elongate device. Elongate device 202 includes a flexible body 216 having proximal end 217 and distal end 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230 may be included as a subsystem of the control system 112. Thus, tracking system 230 may optionally be implemented as hardware, firmware, software or a combination thereof, which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 µm. In other embodiments, the dimensions may be larger or smaller. The optical fiber of shape sensor 222 forms a fiber optic bend sensor for determining the shape of flexible body 216. In one alternative, multiple optical fiber cores including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques.

For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating physiological motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator or other operator with real-time position information. In some examples, the real-time position information may be displayed on display system 110 of FIG. 1 for use by the operator O in the control of medical instrument system 200. In some examples, control system 112 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

Figure 2C:
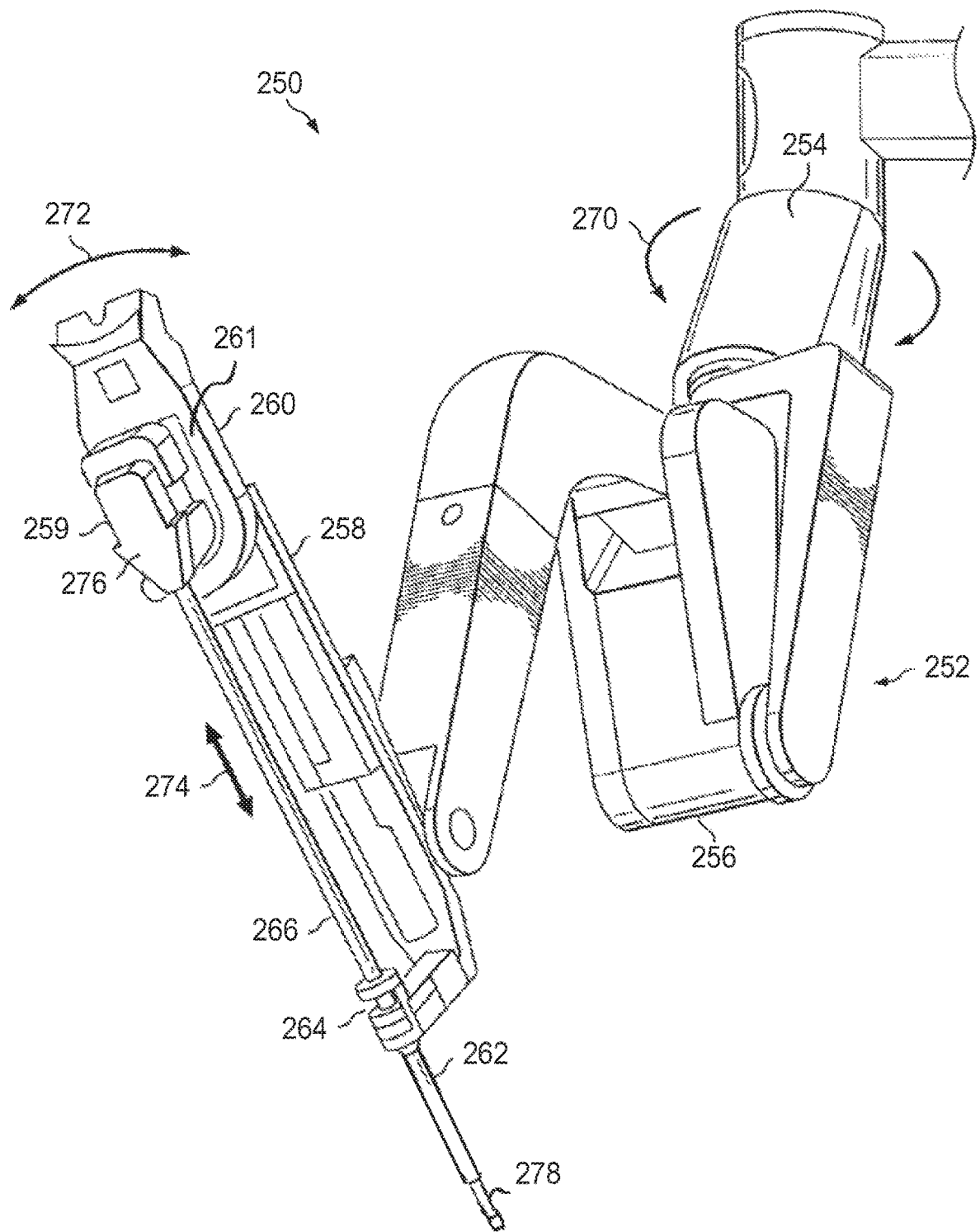
FIG. 2C is a diagram of a medical instrument system with a kinematic chain according to some embodiments.

FIG. 2C illustrates a medical instrument system 250, which may be used as the medical instrument system 104 in a medical procedure performed with teleoperated medical system 100. FIG. 2C is a perspective view of a manipulator 252 of a control arm that may be mounted to or incorporated into the manipulator assembly 102 of FIG. 1. The medical instrument system 250 includes a kinematic chain made up of a plurality of joints. At least some of the joint in the kinematic chain include joint sensors or encoders that can communicate with the control system 112 of FIG. 1 to provide joint sensor data to facilitate monitoring and control of the medical instrument system 250.

The manipulator 252 includes a yaw servo joint 254, a pitch servo joint 256, and an insertion and withdrawal ("I/O") actuator 258. A surgical instrument 259 is shown mounted at an instrument spar 260 including a mounting carriage 261. An illustrative straight cannula 262 is shown mounted to cannula mount 264. Shaft 266 of instrument 259 extends through cannula 262. Manipulator 252 is mechanically constrained so that it moves instrument 259 around a stationary remote center of motion located along the instrument shaft. Yaw servo joint 254 provides yaw motion 270, pitch joint 256 provides pitch motion 272, and I/O actuator 258 provides insertion and withdrawal motion 274 through the remote center. The manipulator 252 may include an encoder to track position and velocity associated with servo positions along the insertion axis of the I/O actuator 258 and other encoders to track position and velocity of yaw servo joint 254 and pitch servo joint 256.

Matching force transmission disks in mounting carriage 261 and instrument force transmission assembly 276 couple actuation forces from actuators in manipulator 252 to move various parts of instrument 259 in order to position and orient a probe 278 mounted at the distal end of the curved shaft 266. Such actuation forces may typically roll instrument shaft 266 (thus providing another DOF through the remote center). The amount of roll may be tracked via an encoder. In alternative embodiments, the instrument 259 may include a wrist at the distal end of the shaft that provides additional yaw and pitch DOF's. The probe 278 may be, for example, a vision probe, such as a stereoscopic imaging catheter having a stereoscopic camera or a three-dimensional, structured light scanner that can be introduced and positioned via the manipulator 252.

In some examples, medical instrument system 200 or the medical instrument system 250 may be teleoperated within the context of the medical system 100 of FIG. 1 as the manipulator assembly 102 or a component thereof. In some embodiments, teleoperational manipulator assembly 102 of FIG. 1 may be replaced by direct operator control. In some examples, the direct operator control may include various handles and operator interfaces for hand-held operation of the instrument.

Figure 3A:
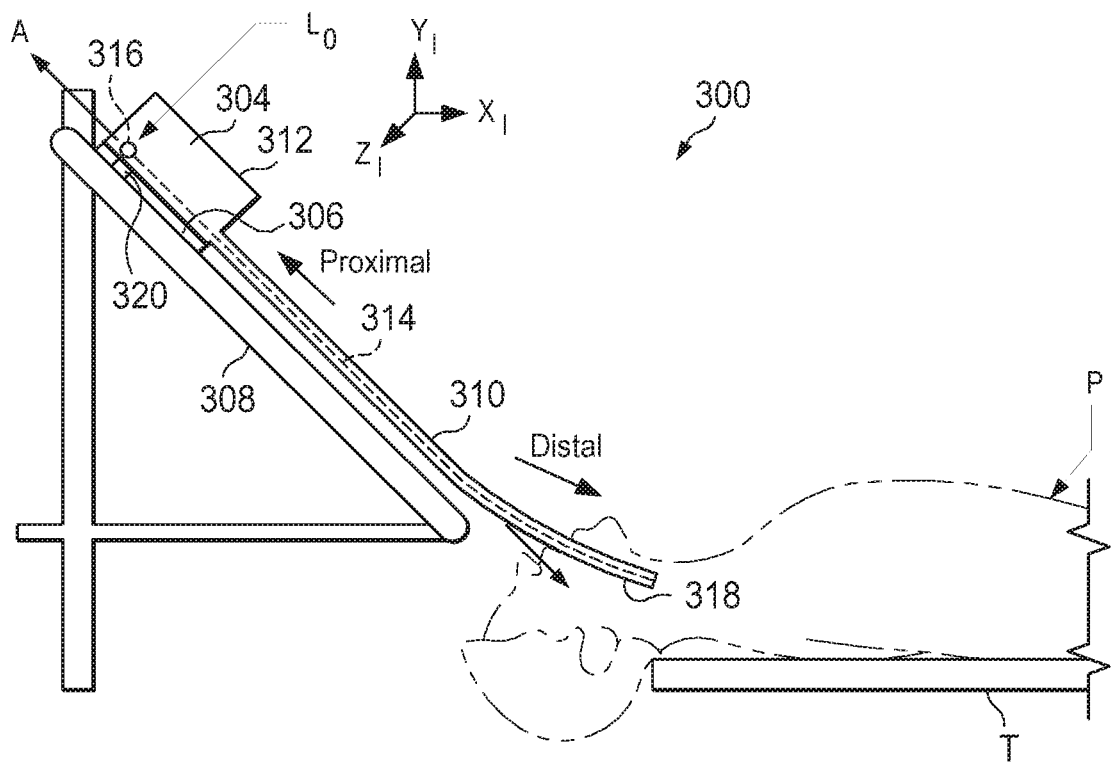
FIGS. 3A and 3B are simplified diagrams of side views of a patient in patient coordinate space including a medical instrument mounted on an insertion assembly according to some embodiments.
Figure 3B:
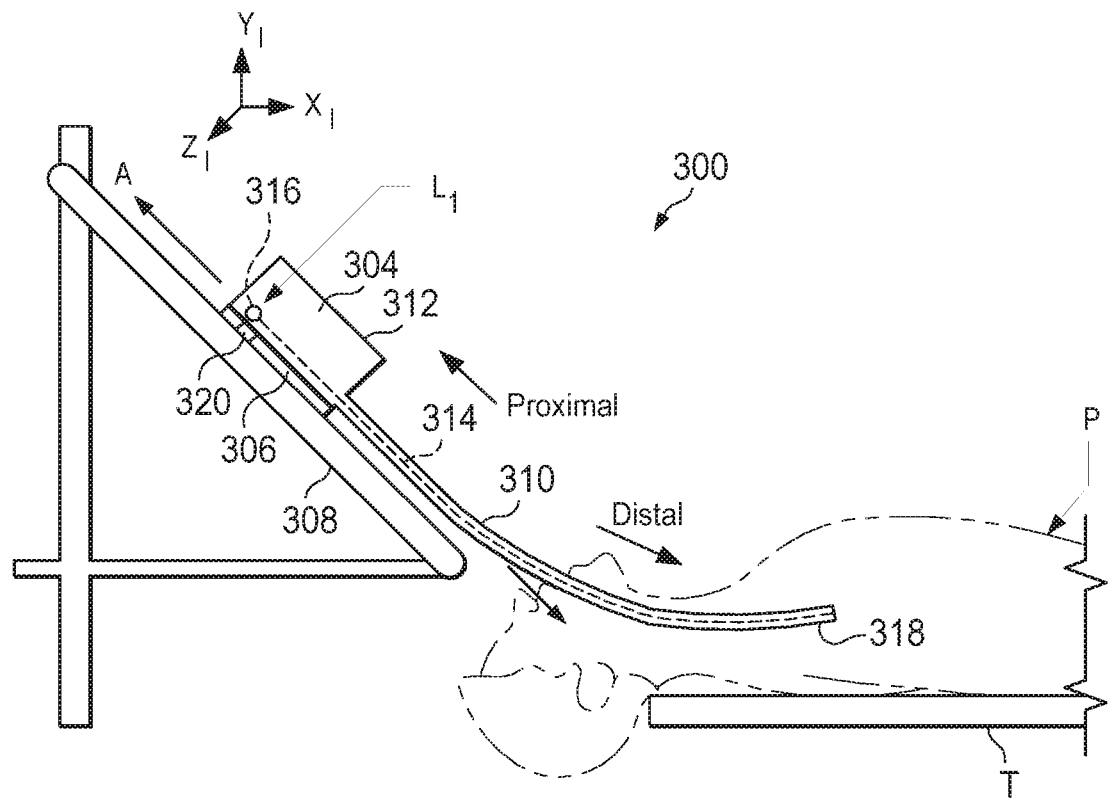

FIGS. 3A and 3B are simplified diagrams of side views of a patient coordinate space including a medical instrument mounted on an insertion assembly according to some embodiments. As shown in FIGS. 3A and 3B, a surgical environment 300 includes the patient P is positioned on the operating table T. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a medical instrument 304 is coupled to an instrument carriage 306. The medical instrument 304 may be provided by the medical instrument system 200 of FIGS. 2A and 2B. In some embodiments, medical instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to medical instrument 304 to control insertion motion (i.e., motion along the A axis) and, optionally, motion of a distal end 318 of an elongate device 310 in multiple directions including yaw, pitch, and roll. The elongate device 310 may be a flexible, steerable catheter. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Medical instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or the another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position $L_0$. In some examples, position $L_x$ may further be used as an indicator of the distance or insertion depth to which distal end 318 of elongate device 310 is inserted into the passageways of the anatomy of patient P.

Figure 4:
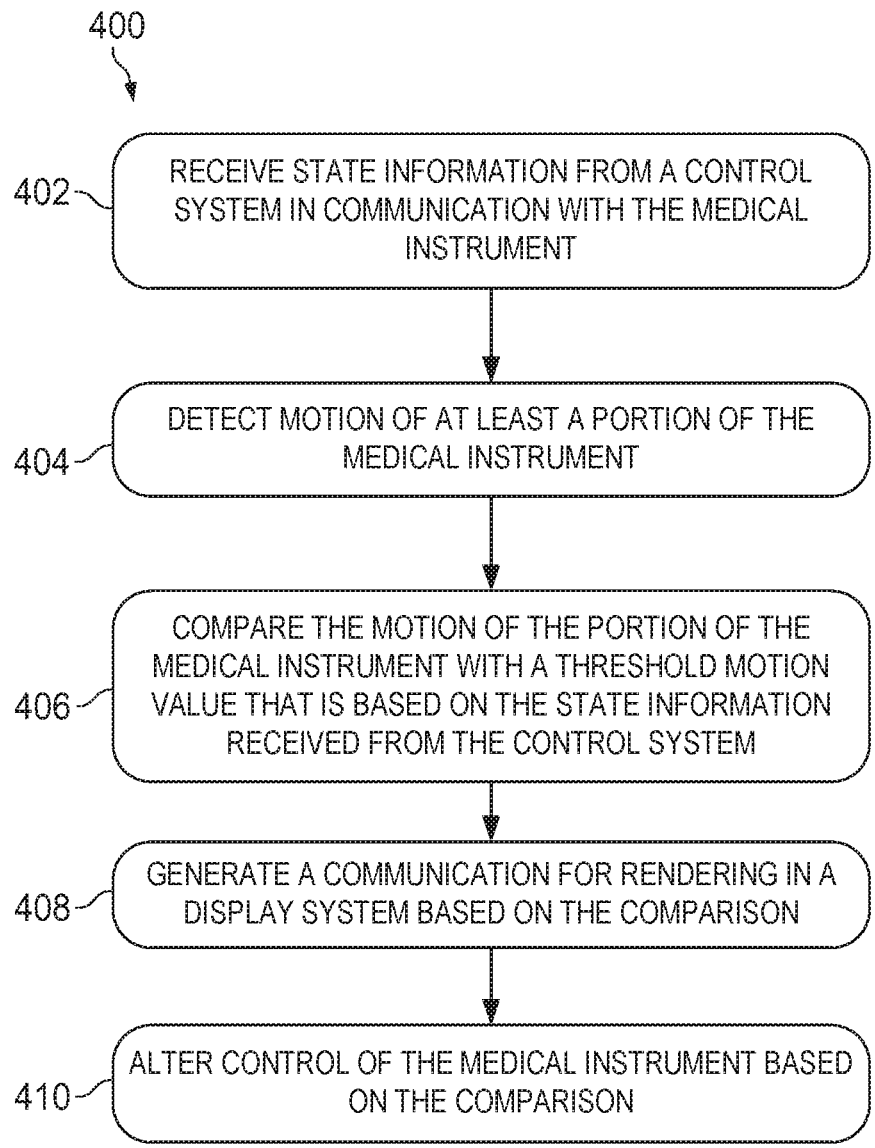
FIG. 4 is a flowchart of a method for monitoring patient movement during a medical procedure according to some embodiments.

FIG. 4 is a flowchart of a method 400 of monitoring patient motion during a medical procedure to detect motion of the patient undergoing the procedure. The method 400 may utilize a medical instrument having a primary purpose other than patient motion monitoring. As illustrated in FIG. 4, the method 400 includes several enumerated steps or operations, which may be performed in the illustrated sequence. Embodiments of the method 400 may include additional or alternative operations before, after, in between, or as part of the enumerated operations. Some embodiments of the method 400 may omit one or more of the enumerated operations. Furthermore, embodiments of the method 400 may include executable instructions stored on a computer-readable medium and executed by a processor, such as a processor of the control system 112 of FIG. 1, to perform the operations of method 400.

Accordingly, an embodiment of the method 400 may begin at operation 402 in which state information may be received from a control system in communication with the medical instrument. At operation 404, the control system may detect motion of at least a portion of the medical instrument. The control system may compare the motion of the portion of the medical instrument with a threshold motion value that is based on the state information received from the control system, at operation 406 to determine patient motion. Based on the determination of patient motion based on the comparison of the detected motion with the threshold motion value, the control system may provide one or more system responses. At operation 408, the control system may generate a communication for rendering in a display system based on the comparison of the motion with the threshold motion value and determination of patient motion. And at operation 410, the control system may alter control of the medical instrument based on the comparison.

To better explain embodiments of the method 400, reference is made herein to additional FIGS. 5A-C and 6A-B, which relate to the positioning of the elongate device 310 of FIGS. 3A and 3B through anatomic passageways 502 of the lungs 500 of the patient P of FIGS. 1 and 3. These passageways 502 include the trachea and the bronchial airways. As shown in FIGS. 3A and 3B, as the carriage 306 moves along the insertion stage 308, the elongate device 310 is advanced within the anatomic passageways 502 of the lungs 500. To navigate the elongate device 310 within the lungs 500, the operator O may steer the distal end 318 of the elongate device 310 while directing the movement of the carriage 306 along the insertion axis A. In navigating through the anatomic passageways 502 (i.e., in a drive state or drive mode), the elongate device 310 assumes a shape that may be measured by the shape sensor 314 extending within the elongate device 310. The control system 112 may also interrogate the shape sensor 314 and/or additional sensors that may provide shape and/or positional information (such as electromagnetic systems and/or joint sensors) when the elongate device 310 is in a parked state or parked mode in which no movement commands are received via the master assembly 106 from the operator O. At operation 402, the state of the medical system 100 may be received by the control system 112 from state information indicating which of several possible states is currently implemented. In addition to the parked state and the drive state, the medical system 100 may have a treatment state in which a medical treatment is being applied to the patient anatomy proximate the distal end 318 of the elongate device 310. For example, the medical treatment may be the insertion of a biopsy needle, an ablation process, a cauterization process, an imaging process, an injection or drug delivery process, or any other medical treatment.

As described herein, in order to navigate to a desired location, the teleoperated medical system 100 may provide real-time imaging to the operator O. The real-time images may be captured images. In some embodiments, an image capture device is positioned at the distal end 318 of the elongate device 310. The real-time images may be simulated or virtual images rendered based on a computer model derived from preoperative images or intraoperative images. The virtual images may depict the elongate device 310 in images that show an external perspective of the patient P. Additionally, the virtual images may depict a representation of the interior surfaces of the passageways 502 of the lung 500 from a perspective determined by the position and orientation of the distal and 318 of the elongate device 310. Such imaging is discussed in more detail in connection with FIGS. 6A and 6B, described further below.

At operation 404, the control system 112 may detect motion of at least a portion of the elongate device 310. Motion may be detected by monitoring for a change in the position of the elongate device 310 over time. For example, the position of the elongate device 310 may be sampled 10 times per second, 100 times per second, or at another suitable frequency. As shown in FIG. 5B, the distal tip 318 of the elongate device 310 has moved from a first position 504A to a second position 504B. This motion may be quantified using information from the fiber optic shape sensor 314, an electromagnetic position sensor, or by comparison of optical images obtained within the anatomical passageways 502. The control system 112 may compare the movement between the first and second positions 504 with a threshold movement value. The threshold movement value may be implemented by the control system 112 to prevent false identification of movement of the distal end 318 as patient movement. For example, due to temperature fluctuations or other minor changes, a change in the indicated position of the distal tip 318, or another portion of the elongate device 310, may be registered without any significant positional change or movement taking place.

As illustrated in FIG. 5B, the threshold movement value may be determined relative to the direction of movement. As shown, lateral movement of the distal tip 318 may have a lateral threshold movement value 506A in a lateral direction, while the insertion/withdrawal (I/O) movement may have an insertion threshold movement value 506B along a direction along the insertion axis of the elongate device. As illustrated, the lateral threshold movement value 506A may be less than the I/O threshold movement value 506B, in some embodiments. Additionally, the magnitude of the threshold movement values 506 may be dependent upon the state of the medical system 100. For example, when the state information received at operation 402 indicates that the medical system 100 (or the manipulator assembly 102 thereof) is in a parked state, the magnitude of the threshold movement values 506 may be smaller than when the state information indicates a drive state. Furthermore, the threshold movement value may be realized as a shape in three-dimensions around the distal tip 318, in some embodiments. Thus, a given movement of the distal tip 318 in Cartesian X, Y, and Z coordinates that moves beyond that three-dimensional threshold may be regarded by the control system 112 as indicative of patient motion. The shape may be circular, ovoid, rectangular, symmetric, asymmetric, or otherwise shaped. The three-dimensional threshold shape may be defined in part by the threshold movement values 506 and be a function thereof. In some embodiments, frequency of detected movement and threshold movement may be quantified and compared alternatively or in addition to magnitude of detected and threshold movements to determine patient motion.

In general, actual movement of the elongate device 310 may occur when the medical system 100 is in the parked state due to cyclical physiological motion, such as respiratory motion in the lung 500. In other embodiments, cardiac motions may be detected from shape/position information obtained from the elongate device 310. Such expected natural motions may be considered by the control system 112 when identifying patient motion. In order to avoid incorrectly triggering the control system 112 to identify motion of the patient P due to expected physiological movement, the threshold movement values 506 associated with the parked state may be sufficient to account for such physiological motion. The shape/position information obtained from the elongate device 310 during the parked state may be used to identify and quantify physiological motion such as from heartbeat or respiration. For example, shape/position information may be collected over a period of time and when identified as cyclical or periodic, can be considered physiological motion. The frequency and/or magnitude of the periodic motion can be used to help determine a value for threshold movement values used to establish patient motion. In additional embodiments, because the effect of physiological motion may depend upon the position of the elongate device 310, the magnitude of the threshold movement values 506 may be based on an insertion depth or a three-dimensional position of the distal tip 318. For example, because the main bronchii of the lungs 500 may move less than the bottom lobe of the lungs 500 during normal respiration, the threshold movement values may be lower when the portion of the elongate device 310 being monitored is positioned within the main bronchii than when it is positioned more deeply in the lungs 500. In alternative embodiments, physiological motion can be detected using separate sensors or equipment such as a respiratory monitor, monitoring an artificial respirator, monitoring an electro-cardiogram of the patient, monitoring thoracic movement of the patient using a movement pad, and/or the like.

As shown in FIG. 5B, the distal tip 318 has moved a distance greater than the lateral threshold movement value 506A. Consequently, when the control system 112 compares the movement of the distal tip 318 with the lateral threshold movement value 506A at operation 406, the control system 112 may detect the movement as indicative of significant movement of the patient P.

Referring now to FIG. 5C, patient motion may be detected during a drive state as well. As noted above, the threshold movement values 506 may be different when the medical system 100 is in a drive state than when the medical system 100 is in a parked state. Additionally, when the medical system 100 is in a parked state as indicated by state information received at operation 402, the control system 112 may receive and analyze movement commands from the operator O as provided via the master assembly 106. For example, prior to receipt of a movement command, the distal tip 318 of the elongate device 310 may be in a first position 508A. A received movement command may be represented by the commanded motion vector 510. In other words, the movement command received from the operator O is intended to and should direct the distal tip 318 (and the trailing portions of the elongate device 310) to move as indicated by the vector 510, e.g. toward the wall at the first branch point in the bronchus.

Instead, the distal tip 318 moves to a second position 508B, as shown in FIG. 5C. This movement may be calculated by the control system 112 as the actual motion vector 512, which is different than the commanded motion vector 510. Because the state information indicates that the medical system 100 is in a drive state, the control system 112 may compare the commanded motion vector 510 with the actual motion vector 512 and determine a difference therebetween. When the difference between the commanded motion vector 510 and the actual motion vector 512 exceeds a threshold motion value, the control system 112 may determine that some motion of patient P has occurred. In some embodiments, actuator current or torque may be measured and compared to the actual motion vector 512. The comparison can be evaluated against a threshold actuator value to determine patient motion. For example, actuators may apply an amount of torque to hold or move the elongate device 310 at or to a desired position. If the elongate device 310 made contact with tissue during patient motion, the amount of torque required for the desired motion would be increased above the threshold actuator value indicating patient movement.

Referring now to FIGS. 6A and 6B, shown therein are images that may be used by the control system 112 to determine a motion of the distal tip 318 of the elongate device 310. FIG. 6A includes an image 600A that represents a virtual view from the distal tip 318. This virtual view is an interior view of a model of the lungs 500, such as a surface model derived from preoperative or intraoperative medical images, such as a CT scan. FIG. 6B includes an image 600B that represents an actual view obtained by an image capture device positioned at the distal tip 318 of the elongate device 310 positioned within lungs 500. The control system 112 may select to the virtual view of image 600A based on the state indicated by the received state information, in some embodiments. For example, when the medical system 100 is in a parked state, a position and orientation of the distal tip 318 of the elongate device 310 may be used to generate a virtual view of the three-dimensional surface model of the lungs from the perspective indicated by the position and orientation. When the medical system 100 is in a drive state, the control system 112 may generate and use a predicted perspective of the distal tip 318, so that the actual image 600B may be compared with the portion of the surface model that should be in view at a given time based on the commanded motion of the distal tip 318. The control system 112 may utilize image processing techniques to compare the virtual view of the image 600A with the actual view of the image 600B. Depending on the relationship between the images 600, the control system 112 may be able to estimate a difference in the perspectives therebetween.

In some embodiments, the control system 112 may search the model to find an image best corresponding to the actual image 600B and then calculate a difference in position and orientation therebetween. The position of the expected image 600A and the position of the searched-for image identified in the model corresponding best to the actual image 600B may be calculated by the control system 112. Additionally, the control system 112 may compare the actual image 600B with the virtual image 600A to determine a difference in position and/or orientation therebetween. The difference in position may be used by the control system 112 to determine a motion of the distal tip 318. This motion may then be compared with a threshold motion value to determine whether the patient P has moved significantly.

In some embodiments, both the images 600A and 600B may be actual images. For example, the image 600A may be an image obtained before a degree of motion is detected while the image 600B may be an image obtained after that degree of motion is detected. The control system 112 may compare the images 600 with virtual views obtained from the model of the lungs 500. For example, the control system 112 may utilize the images 600 to search for matching images provided by virtual views in an area close to the distal tip 318. When matches of both the images 600 are identified, a vector between positions associated with the matched images in the model of lungs 500 may be used to identify motion of the distal tip 318. This identified motion vector may be compared with a threshold motion value in an embodiment of the operation 406 of method 400 to determine significant patient movement.

In some additional embodiments, more than one motion sensing modality may be used in detecting patient motion in order to improve accuracy. For example, information from both the shape sensor 314 (a first motion detecting modality) and image processing (a second motion detecting modality) may be used to determine that a patient motion has occurred. In some embodiments, thresholds may be set such that if either of two sensing modalities indicates motion, then the control system 112 takes steps to mitigate the motion. Additionally, other embodiments may include thresholds that are lower and are required to be exceeded for multiple modalities before the control system 112 identifies patient motion.

As described herein, reference is frequently made to motion of the patient P. Some embodiments of the present disclosure provide for the detection of motion of the patient P relative to the patient coordinate frame, the detection of motion of a portion of the patient P with respect to another portion (e.g., motion of the lungs relative to the trachea), and/or the detection of motion of the patient P relative to the medical system 100 itself. Some other embodiments of the present disclosure provide for the detection of motion of the patient P by detecting motion of the medical system 100 relative to the patient P. Thus, motion of the patient P as used herein may refer to relative motion between the body of the patient P and the medical instrument 104 and/or the manipulator assembly 102, regardless of whether it is the body of the patient P that moves or whether it is the medical instrument 104 or manipulator 102 that moves.

In some instances, the operator O or another person present in the vicinity of the medical instrument 104 and/or the manipulator assembly 102 may cause motion of the medical instrument 104 and/or the manipulator assembly 102. For example, the operator O may accidentally bump the instrument 104, causing motion of the distal tip of the elongate device 310. This accidental bumping of the instrument 104 may thus be interpreted by the control system 112 as patient motion. The control system 112 may automatically perform one or more operations to prevent harm from resulting from this patient motion. For example, the operator O may bump the medical instrument system 250 of FIG. 2C. The encoders at the servo joints 254 and 256 may report motion or a change in position to the control system 112. That motion would be compared with expected motion, whether in a parked state or a drive state, to determine whether or not the patient has moved. Thus, motion of components of the medical system 100 relative to patient P may be detected and responded to by the control system 112 as motion of the patient P.

Referring now to FIG. 7, an exemplary endotracheal (ET) tube 700 is illustrated as positioned within the patient P to facilitate insertion of the elongate device 310 into the lungs 500 of the patient P. A cross-sectioned portion 702 shows a portion of the elongate device 310 extending within the ET tube 700. The geometry of the ET tube 700 may be provided to the control system 112 so that a bend 704 of the ET tube 700 may be known to the control system 112. Even if a bend 704 in the tube is not precisely known, the curvature may be sufficiently distinctive to be identified in shape data as corresponding to the upper respiratory track and trachea because the portion of the elongate device 310 at the proximal end of the ET tube 700 forms a known angle (nearly 90°) with respect to the portion of the elongate device 310 at the distal end of the ET tube 700. The pose of the proximal end of the elongate device 310 may be known due to sensors extending therein, like the optical fiber shape sensor 314 in the illustrated embodiment. Based on this shape information and known curvature of the ET tube 700, the trachea of the patient P may be identified. During a medical procedure within the lungs, the trachea of the patient P may be unlikely to move due to the presence of the elongate device 310. Accordingly, the portion of the elongate device 310 positioned within the ET tube 700 at any given time may be monitored in order to identify any motion of the patient P. When motion of this portion of the elongate device 310 is detected by the control system 112, the motion is likely to be interpreted by the control system 112 as indicative of patient motion. In other words, a threshold motion value associated with the endotracheal tube 700 may be smaller than a threshold motion values used to detect patient motion at the distal tip 318 of the elongate device 310.

Some embodiments of the ET tube 700 may include a known shape feature, such as the perturbation 706 shown near the distal end of the ET tube 700. The perturbation 706 may be a small undulation or other feature that may be readily detected by the control system 112 from the shape information received from the elongate device 310. In such embodiments, the portion of the elongate device 310 disposed within the perturbation 706 may be monitored to detect patient motion as described herein. Other embodiments of the method 400 of FIG. 4 may rely on other structures in detecting motion of at least a portion of the medical instrument that is indicative of patient motion.

Returning again to FIG. 4, after motion of the portion of the medical instrument as compared with a threshold motion value or several threshold motion values, the control system 112 may generate a communication or message for rendering or presentation in the display system 110 based on the comparison and determination of significant patient movement performed at operation 406. At operation 408, the message may be generated and rendered in a display as shown in FIG. 8. FIG. 8 depicts an embodiment of the display system 110 which includes a rendering of a graphical user interface 800. As shown in FIG. 8, the user interface 800 includes a rendering of the lungs 500, which may be a surface model derived from preoperative or intraoperative image data or a rendering of the image data itself. A model of the elongate device 310 is also rendered in the illustrated embodiment of the user interface 800. An exemplary communication, patient motion message 802, may be overlaid on the user interface 800 to communicate to the operator O that the patient P has moved or is likely to have moved is determined by the control system 112. For example, the patient motion message 802 may include text (e.g. "Warning: patient motion detected!") and/or graphical elements to communicate to the operator O. In some embodiments, the message may be displayed as a moving message or graphic across the bottom, middle, or top of a display. The patient motion message 802 may include one or more graphical user interface elements associated with options to be presented to the operator O. For example, the patient motion message 802 may include an interface element (e.g., a selectable button) associated with an option 804A whereby the operator O may request that the control system 112 discard the existing registration and perform a new registration between the lungs 500 and a model of the lungs 500. Selecting the option 804A may also comprise a request to update an existing registration. The message 802 may include displaying a numerical value (or a graphical representation of the numerical value) indicating a detected magnitude of patient motion based on sensor measurements and/or differences in sequential images. In some embodiments, the patient motion message 802 may include an interface element associated with an option 804B, the selection of which may cause the control system 112 to resume operation without updating the registration or performing a new registration.

Other communications or messages may be generated by the control system 112. For example, the control system 112 may cause the screen or an element on the screen to flash or pulse. The message may include a sound emitted from a speaker coupled to the control system 112, such as an alarm sound or a verbal message. The message may be interactive and provide options of some actions the operator O may take (for example, request an update to a registration or request a new registration) or to ignore the detected motion. In some implementations, the control system 112 may ignore or filter out any movement commands or end effector actuation commands, until the physician O acknowledges the alert message by pushing a physical button, a virtual button, or speaks a verbal command.

Some implementations of the method 400 may include an operation that identifies a magnitude of the difference between the motion of the portion of the medical instrument and the threshold motion value or values. A threshold control value may be applied such that ignoring the patient motion message 802 by selecting the option 804B is permitted by the control system 112 only when the difference is below the threshold control value. When the difference is greater than a threshold control value, the option 804B may not be presented to the operator O. Accordingly, a first intervention may be implemented by the control system 112 when a first level of difference is detected, while a second intervention may be implemented by the control system 112 when a second, higher level of difference is detected. Additionally, when the difference exceeds the threshold control value, the control system 112 may alter control of the medical instrument at operation 410. For example, the control system 112 may ignore subsequent motion commands received from the master assembly 106 until a new registration is performed or an existing registration is updated. In this manner, the control system 112 may prevent the operator O from relying on a registration that is likely to be unreliable due to a relatively large motion of the patient P or of the medical system 100. Similarly, any commands associated with the performance of a treatment, such as the performance of a biopsy with a biopsy needle protruding from the distal tip 318, may be ignored until a reliable registration is provided to compensate for the motion of the patient P.

One of ordinary skill in the art may be able to identify combinations of disclosed embodiments and additional features that are within the scope of the present disclosure. Accordingly, the spirit and scope of the present disclosure may be best understood by reference to the following claims.

What is claimed is:

1. A method of monitoring a medical instrument during a medical procedure involving motion of the medical instrument, the method comprising:
    receiving state information from a control system in communication with the medical instrument;
    detecting, by the control system, motion of at least a portion of the medical instrument;
    comparing the detected motion of the at least the portion of the medical instrument with a threshold motion value that is based on the state information received from the control system;
    determining, based on the detected motion of the at least the portion of the medical instrument exceeding the threshold motion value, significant movement of a patient has occurred;
    providing a system response based on the determining significant movement of the patient has occurred;
    comparing the detected motion of the at least the portion of the medical instrument with a threshold control value, wherein the threshold control value is higher than the threshold motion value; and
    disregarding, when the detected motion is higher than the threshold control value, motion commands received from a master assembly.

2. The method of claim 1, further comprising:
    generating, when the detected motion is higher than the threshold motion value, a message for presentation in a display system.

3. The method of claim 1, wherein the system response includes disregarding commands received from the master assembly based on the determining significant movement of the patient has occurred.

4. The method of claim 1, wherein detecting motion of the at least the portion of the medical instrument comprises:
    detecting motion by a first motion detection modality; and
    detecting motion by a second motion detection modality, and
    the method further comprises comparing motion detected by the first motion detection modality with motion detected by the second motion detection modality.

5. The method of claim 4, wherein comparing motion includes comparing an image of an interior of an anatomy with a virtual view derived from a model of the anatomy.

6. The method of claim 1, wherein the state information includes an indication the medical instrument is in a parked state and the threshold motion value is further based on an expected natural motion of the patient.

7. A medical system comprising:
an elongate medical instrument;
a master assembly configured to receive commands from an operator to manipulate the medical instrument; and
a control system in communication with the master assembly and the medical instrument,
the control system adapted to perform operations comprising:
receiving state information;
detecting motion of at least a portion of the medical instrument with a first motion detection modality and a second motion detection modality;
comparing the detected motion of the at least the portion of the medical instrument with a threshold motion value that is based on the state information; and
determining, based on the detected motion of the at least the portion of the medical instrument exceeding the threshold motion value, significant movement of a patient has occurred.

8. The medical system of claim 7, further comprising a display configured to present a message based on the comparison of the detected motion with the threshold motion value; and
wherein the operations further comprise comparing the detected motion of the at least the portion of the medical instrument with a threshold control value, wherein the threshold control value is higher than the threshold motion value.

9. The medical system of claim 8, wherein:
the message is presented when the detected motion is higher than the threshold motion value; and
the master assembly is further configured to disregard the commands from the operator when the detected motion is higher than the threshold control value.

10. The medical system of claim 7, wherein the threshold motion value comprises a first threshold motion detection value and a second threshold motion detection value.

11. The medical system of claim 7, wherein:
the first motion detection modality comprises at least one of an electromagnetic sensor or a fiber optic shape sensor extending along a length of the medical instrument; and
the second motion detection modality comprises an image capture device disposed at a distal tip of the medical instrument.

12. The medical system of claim 7, wherein the medical instrument comprises a position sensor, and wherein the medical system comprises at least one actuator configured to control the medical instrument.

13. The medical system of claim 12, wherein the position sensor comprises at least one of an electromagnetic sensor or an optical fiber shape sensor extending a length of the medical instrument.

14. The medical system of claim 12, wherein detecting motion of the at least the portion of the medical instrument comprises:
detecting motion by the position sensor; and
detecting motion by the at least one actuator, and
the operations further comprise comparing motion detected by the position sensor with motion detected by the at least one actuator.

15. The medical system of claim 7, wherein:
the medical instrument comprises an image capture device disposed at a distal tip of the medical instrument; and
the image capture device is configured to capture an image of an interior of an anatomy of the patient.

16. The medical system of claim 15, wherein detecting motion of the at least the portion of the medical instrument comprises comparing the image of the interior of the anatomy with a virtual image derived from a model of the anatomy.

17. The medical system of claim 7, wherein the state information comprises at least one of an indication of a medical instrument parked state, an indication of a medical instrument drive state, an indication of a medical instrument treatment state, or sensor data from a sensor disposed along a kinematic chain associated with the elongate medical instrument.

18. The medical system of claim 7, wherein the state information comprises an indication that the medical instrument is in a parked state, and wherein the threshold motion value is further based on an expected natural motion of the patient when the state information indicates the medical instrument is in the parked state.

19. A method of monitoring a medical instrument during a medical procedure involving motion of the medical instrument, the method comprising:
receiving state information from a control system in communication with the medical instrument, wherein the state information includes an indication the medical instrument is in a parked state;
detecting, by the control system, motion of at least a portion of the medical instrument;
comparing the detected motion of the at least the portion of the medical instrument with a threshold motion value that is based on the state information received from the control system and an expected natural motion of a patient; and
providing a system response based on the comparison of the detected motion with the threshold motion value.

* * * * *